US008802735B2

(12) United States Patent
Hauck

(10) Patent No.: US 8,802,735 B2
(45) Date of Patent: Aug. 12, 2014

(54) (Z)-2-CYANO-3-HYDROXY-BUT-2-ENOIC ACID-(4'-TRIFLUORMETHYLPHENYL)-AMIDE TABLET FORMULATIONS WITH IMPROVED STABILITY

(75) Inventor: Gerrit Hauck, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/422,494

(22) Filed: Mar. 16, 2012

(65) Prior Publication Data

US 2012/0208880 A1  Aug. 16, 2012

Related U.S. Application Data

(63) Continuation-in-part of application No. PCT/EP2010/063439, filed on Sep. 14, 2010.

(60) Provisional application No. 61/363,382, filed on Jul. 12, 2010.

(30) Foreign Application Priority Data

Sep. 18, 2009 (EP) ..................................... 09290716

(51) Int. Cl.
*A01N 37/18* (2006.01)
*A61K 9/20* (2006.01)
*A61K 31/277* (2006.01)

(52) U.S. Cl.
CPC ............. *A61K 31/277* (2013.01); *A61K 9/2059* (2013.01); *A61K 9/2054* (2013.01); *A61K 9/2013* (2013.01)
USPC ............................ 514/627; 424/464; 558/464

(58) Field of Classification Search
USPC ............................ 424/464; 514/627; 558/375
See application file for complete search history.

(56) References Cited

U.S. PATENT DOCUMENTS

| 4,965,276 | A | 10/1990 | Bartlett et al. |
| 5,459,163 | A | 10/1995 | Bartlett et al. |
| 5,679,709 | A | 10/1997 | Bartlett et al. |
| 5,990,141 | A | 11/1999 | Hirth et al. |
| 6,133,301 | A | 10/2000 | Bartlett |
| 6,794,410 | B2 * | 9/2004 | Wettstein ....................... 514/521 |
| 2005/0158371 | A1 | 7/2005 | Nishikado et al. |

| 2005/0220874 | A1 * | 10/2005 | Han et al. ....................... 424/468 |
| 2006/0024376 | A1 | 2/2006 | Williams |
| 2012/0172427 | A1 * | 7/2012 | Hauck ........................... 514/521 |

FOREIGN PATENT DOCUMENTS

| CA | 2443285 | 8/2007 |
| WO | WO 02/080897 A1 | 10/2002 |
| WO | WO 2007/118684 A1 | 10/2007 |

OTHER PUBLICATIONS

Manna, et al., Immunosuppressive Leflunomide Metabolite (A77 1726) Blocks TNF-Dependent Nuclear Factor-KB Activation and Gene Expression, J. Immunol., (1999), vol. 162, pp. 2095-2102.
International Search Report for WO2011/032929 dated Mar. 24, 2011.
Bruneau, et al., Purification of Human Dihydro-Orotate Dehydrogenase and Its Inhibition by A77 1726, the Active Metabolite of Leflunomide, Biochem. J., (1998), pp. 299-303, vol. 336.
Cherwinski, et al., The Immunosuppressant Leflunomide Inhibits Lymphocyte Progression Through Cell Cycle by a Novel Mechanism, J. Pharmacol. Exp. Therap., (1995), pp. 460-468, vol. 272, No. 1.
Fujita, et al., Generation of Formaldehyde by Pharmaceutical Excipients and Its Absorbtion by Meglumine, Chemical & Pharmaceutical Bulletin, vol. 57, No. 10, pp. 1096-1099, (2009).
Prakash, et al., Leflunomide, A Review of its Use in Active Rheumatoid Arthritis, Drugs (1999), pp. 1137-1184, vol. 53, No. 6.
Rowe, et al., Colloidal Silicon Dioxide, Handbook of Pharmaceutical Excipients, pp. 188-190, (2006).
Bartlett, et al., Leflunomide (HWA 486). A Novel Immunomodulating Compound for the Treatment of Autoimmune Disorders and Reactions Leading to Transplantation Rejection, Agents and Actions, vol. 32, No. 1/2, (1991), pp. 10-21.
Aulton, Tablet Excipients, Pharmacetics—The Science of Dosage Form Design, (2002), pp. 404-410.
Knuniants, I.L., Chemical Encyclopedia, vol. 1, (1988), p. 406-407.
Guedas, et al., Tecnologia Farmaceutica, Cuarta Edicion. Editorial Acribia Zaragoza (Espana), p. 301, (1981).

* cited by examiner

*Primary Examiner* — Ali Soroush
(74) *Attorney, Agent, or Firm* — Jiang Lin

(57) ABSTRACT

The invention relates to solid pharmaceutical compositions comprising (Z)-2-cyano-3-hydroxy-but-2-enoic acid-(4'-trifluoromethylphenyl)-amide, as well as a process for the preparation of the same, methods of using such compositions to treat subjects suffering from autoimmune diseases in particular systemic lupus erythematosus or chronic graft-versus-host disease, multiple sclerosis or rheumatoid arthritis.

37 Claims, No Drawings

(Z)-2-CYANO-3-HYDROXY-BUT-2-ENOIC ACID-(4'-TRIFLUORMETHYLPHENYL)-AMIDE TABLET FORMULATIONS WITH IMPROVED STABILITY

The present application is a Continuation-in-Part of International Application No. PCT/EP2010/063439, filed Sep. 14, 2010, which claims the benefit of U.S. Provisional Application No. 61/363,382, filed Jul. 12, 2010, both of which are incorporated herein by reference in their entireties.

FIELD OF THE INVENTION

The present invention relates to pharmaceutical compositions comprising (Z)-2-cyano-3-hydroxy-but-2-enoic acid-(4'-trifluoromethylphenyl)-amide, commonly known as Teriflunomide, as well as a process for the preparation of the same, methods of using such compositions to treat subjects suffering from autoimmune diseases in particular systemic lupus erythematosus or chronic graft-versus-host disease or multiple sclerosis or rheumatoid arthritis.

BACKGROUND OF THE INVENTION (Z)-2-cyano-3-hydroxy-but-2-enoic acid-(4'-trifluoromethylphenyl)-amide (Teriflunomide) has the structure illustrated in Formula I:

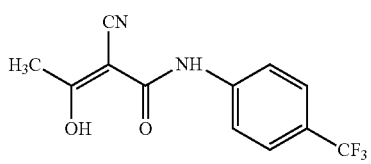

Formula I (Z)-2-cyano-3-hydroxy-but-2-enoic acid-(4'-trifluoromethylphenyl)-amide (Teriflunomide, Formula I) use in treating chronic graft-versus-host disease has been disclosed in U.S. Pat. No. 4,965,276 issued on Oct. 23, 1990. U.S. Pat. No. 5,459,163 issued on Oct. 21, 1997 and U.S. Pat. No. 5,679,709 issued on Oct. 21, 1997 disclose compositions useful for treating autoimmune diseases in particular lupus erythematosus. Teriflunomide has been shown to produce antiproliferative effects on a wide variety of immune cells and cell lines (Cherwinski H. M., et al., J. Pharmacol. Exp. Ther. 1995; 272:460-8; Prkash A., et al., Drugs 1999; 58(6):1137-66; Bartlett R. R. et al., Agent Action 1991; 32(1-2):10-21). Additionally, it inhibits the enzyme dihydroorotate dehydrogenase, an enzyme essential for the synthesis of pyrimidines (Bruneau J-M, et al., Biochem. J. 1998; 36:299-303). European Patent 1381356 B1 discloses the use of Teriflunomide for the manufacture of a medicament for treating multiple sclerosis wherein said medicament is administered orally. International Application WO 2007/118684 discloses Leflunomide containing solid pharmaceutical compositions including an organic or inorganic acid characterized by improved stability. Said compositions show a slighter decomposition of Leflunomide to Teriflunomide than in commercial Arava® tablets. Teriflunomide amounts are disclosed which range from 0.02 mg to 0.511 mg per tablet containing 10 mg of Leflunomide. These are less than 0.35% Teriflunomide with respect to the total mass of the tablet, which is 150 mg.

A solid pharmaceutical formulation for Teriflunomide was developed for use in clinical studies. One of the observations made during stability studies was a strong increase in one degradant, which is 2-cyano-N-(4-trifluoromethyl-phenyl)-acetamide and has the structure illustrated in Formula II:

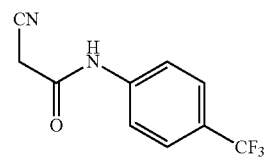

Formula II

At room temperature storage 2-cyano-N-(4-trifluoromethyl-phenyl)-acetamide levels of up to 0.2% are reached in the solid pharmaceutical formulation after 12 month storage [Teriflunomide 7 mg tablets, Al/PVC blisters, storage at 25±2° C. and 60% relative humidity {RH}]. A further degradant could be 4-trifluoromethyl-aniline.

It is an object of the present invention to find a solid pharmaceutical formulation for Teriflunomide which does not have the disadvantages of increased concentrations of 2-cyano-N-(4-trifluoromethyl-phenyl)-acetamide or 4-trifluoromethyl-aniline (4-TFMA).

It has been found that some solid pharmaceutical formulations for Teriflunomide without colloidal silicon dioxide do not have the disadvantages mentioned which is limited increase in 2-cyano-N-(4-trifluoromethyl-phenyl)-acetamide formation and limited formation of 4-TFMA It has further been found advantageous to add an acidic reacting compound to said solid pharmaceutical formulation for Teriflunomide without colloidal silicon dioxide.

It has also been additionally found advantageous to add an acid reacting compound to solid formulations of Teriflunomide containing colloidal silicon dioxide.

SUMMARY OF THE PRESENT INVENTION

The present invention is a solid pharmaceutical composition comprising about 1% to 30% weight:weight (w:w) Teriflunomide, or a pharmaceutically acceptable basic addition salt thereof, about 5% to 20% weight:weight disintegrant, about 0% to 40% weight:weight binder, about 0.1% to 2% weight:weight lubricant and the remaining percentage comprising diluents provided that said solid pharmaceutical composition does not contain colloidal silicon dioxide.

A second aspect of the invention is a solid pharmaceutical composition comprising about 1% to 20% weight:weight Teriflunomide, or a pharmaceutically acceptable basic addition salt thereof, about 5% to 20% weight:weight disintegrant, about 0% to 30% weight:weight binder, about 0.1% to 2% weight:weight lubricant, about 1% to 20% weight:weight acidic reacting compound and the remaining percentage comprising diluents.

A third aspect of the invention is a solid pharmaceutical composition comprising about 1% to 20% weight:weight Teriflunomide, or a pharmaceutically acceptable basic addition salt thereof, about 5% to 20% weight:weight disintegrant, about 0% to 30% weight:weight binder, about 0.1% to 2% weight:weight lubricant, about 1% to 20% weight:weight acidic reacting compound, about 0.1% to 0.5% weight:weight colloidal silicon dioxide and the remaining percentage comprising diluents.

DETAILED DESCRIPTION OF THE INVENTION

The preparation according to the invention therefore provides a solid pharmaceutical composition comprising a) about 1% to 30% weight:weight Teriflunomide, or a pharmaceutically acceptable basic addition salt thereof,
b) about 5% to 20% weight:weight disintegrant,
c) about 0% to 40% weight:weight binder,
d) about 0.1% to 2% weight:weight lubricant and
e) the remaining percentage comprising diluents, provided that said solid pharmaceutical composition does not contain colloidal silicon dioxide.

Terms used herein have the meanings defined in this specification.

"Colloidal silicon dioxide" is submicroscopic fumed silica, also known as pyrogenic silica. It is a non-crystalline, fine grain, low density and high surface area silica. Primary particle size is from 5 nm to 50 nm. The particles are non-porous and have a surface from 50 $m^2$/g to 600 $m^2$/g. It can be obtained for example under the trade name Aeorsil 200 Pharma from Evonik Industries [Evonik Degussa GmbH, Inorganic Materials, Weissfrauenstraβe 9, 60287 Frankfurt, Germany] or under the trade name CAB-O-SIL M-5P/5DP Cabot Corporation headquartered at Boston, Mass., U.S.A.

"Degradant" refers to any drug-based materials generated after the preparation of the unit dosage form. Analysis of impurities and degradant is done using reverse phase HPLC techniques on extracted samples as is known in the art.

"Pharmaceutically acceptable basic addition salt" is any non-toxic organic or inorganic basic addition salt of the compound Teriflunomide. Illustrative inorganic bases which form suitable salts include potassium hydroxide, sodium hydroxide, L-lysine or calcium hydroxide.

"Patient" means a warm blooded animal, such as for example rat, mice, dogs, cats, guinea pigs, and primates such as humans.

"Treat" or "treating" means any treatment, including, but not limited to, alleviating symptoms, eliminating the causation of the symptoms either on a temporary or permanent basis, or preventing or slowing the appearance of symptoms and progression of the named disorder or condition.

"Therapeutically effective amount" means an amount of the compound, which is effective in treating the named disorder or condition.

"Stereoisomers" is a general term for all isomers of the individual molecules that differ only in the orientation of their atoms in space. It includes mirror image isomers (enantiomers), geometric (cis/trans) isomers, and isomers of compounds with more than one chiral center that are not mirror images of one another (diastereoisomers).

"Teriflunomide" is the generic name for the compound (Z)-2-cyano-3-hydroxy-but-2-enoic acid-(4'-trifluoromethylphenyl)-amide. Teriflunomide can be used in the form in which it is chemically prepared, or it can be subjected to a process which changes the physical nature of the particles. For example, the material can be milled by any process known in the art. Non exclusive examples of such processes include mechanical milling and jet milling. The particles produced either directly from the process of chemically preparing Teriflunomide or after a milling operation preferably provide average particle diameters in the range of 1 μm to 100 μm. It is advantageous to use said Teriflunomide particles from 1 μm to 100 μm in the preparation of the solid pharmaceutical composition, especially at about 1% to 10% weight:weight of Teriflunomide.

The synthesis of Teriflunomide has been disclosed, and is accomplished by methods that are well known to those skilled in the art. For example, U.S. Pat. No. 5,990,141, issued on Nov. 23, 1999 discloses methods of synthesis.

In a further embodiment the invention relates to a solid pharmaceutical composition comprising a therapeutically effective amount of teriflunomide or a pharmaceutically acceptable basic addition salt thereof, wherein the solid pharmaceutical composition does not contain colloidal silicon dioxide.

In a further embodiment the invention relates to a solid pharmaceutical composition comprising from about 2% to 15% weight:weight Teriflunomide and the other components disintegrant, binder, lubricant and diluents show the same amount as defined under b) to e) above.

In a further embodiment the invention relates to a solid pharmaceutical composition comprising from about 7% to 15% weight:weight disintegrant and the other components Teriflunomide, binder, lubricant and diluents show the same amount as defined under a) and c) to e) above.

In a further embodiment the invention relates to a solid pharmaceutical composition comprising from about 15% to 35% weight:weight binder and the other components Teriflunomide, disintegrant, lubricant and diluents show the same amount as defined under a), b), d) and e) above.

In a further embodiment the invention relates to a solid pharmaceutical composition comprising from about 0.1% to 1.0% weight:weight lubricant and the other components Teriflunomide, disintegrant, binder and diluents show the same amount as defined under a) to c) and e) above.

Examples of disintegrants are carboxymethylcellulose, low substituted hydroxyproyl cellulose, microcrystalline cellulose, powdered cellulose, croscarmellose sodium, methylcellulose, polacrilin potassium, sodium alginate, sodium starch glycolate or a mixture of one or more of said disintegrants.

Examples of binders are acacia, carboxymethylcellulose, hydroxyethylcellulose, hydroxypropylcellulose, dextrin, gelatin, guar gum, hydroxypropyl methylcellulose, maltodextrin, methylcellulose, sodium alginate, pregelatinized starch, starches such as potato starch, corn starch or cereal starch and zein or a mixture of one or more of said binders.

Examples of lubricants are calcium stearate, glyceryl palmitostearate, sodium benzoate, sodium lauryl sulfate, sodium stearyl fumarate, stearic acid, talc, zinc stearate and magnesium stearate or a mixture of one or more of said lubricants.

Examples of diluents are cellulose, cellulose acetate, dextrates, dextrin, dextrose, fructose, 1-O-α-D-Glucopyranosyl-D-mannitol, glyceryl palmitostearate, hydrogenated vegetable oil, kaolin, lactitol, lactose, lactose mono-hydrate, maltitol, mannitol, maltodextrin, maltose, pregelatinized starch, sodium chloride, sorbitol, starches, sucrose, talc and xylitol or a mixture of one or more of said diluents.

In a further embodiment the invention relates to a solid pharmaceutical composition comprising from 2% to 15% weight:weight Teriflunomide, 7% to 15% weight:weight disintegrant selected from one or more of microcrystalline cellulose or sodium starch glycolate, 15% to 35% weight:weight binder selected from one or more of hydroxyproylcellulose or corn starch, 0.1% to 1.0% weight:weight lubricant selected from magnesium stearate and the remaining percentage comprising diluents selected from lactose mono-hydrate.

In a further embodiment the invention relates to a solid pharmaceutical composition comprising
A) about 1% to 20% weight:weight Teriflunomide, or a pharmaceutically acceptable basic addition salt thereof,
B) about 5% to 20% weight:weight disintegrant,
C) about 0% to 30% weight:weight binder,
D) about 0.1% to 2% weight:weight lubricant,
E) about 1% to 20% weight:weight acidic reacting compound and
F) the remaining percentage comprising diluents.

In a further embodiment the invention relates to a solid pharmaceutical composition comprising from about 2% to 15% weight:weight Teriflunomide and the other components disintegrant, binder, lubricant, acidic reacting compound and diluents show the same amount as defined under B) to F) above.

In a further embodiment the invention relates to a solid pharmaceutical composition comprising from about 7% to 15% weight:weight disintegrant and the other components Teriflunomide, binder, lubricant, acidic reacting compound and diluents show the same amount as defined under A) and C) to F) above.

In a further embodiment the invention relates to a solid pharmaceutical composition comprising from about 15% to 30% weight:weight binder and the other components Teriflunomide, disintegrant, lubricant, acidic reacting compound and diluents show the same amount as defined under A), B) and D) to F) above.

In a further embodiment the invention relates to a solid pharmaceutical composition comprising from about 0.1% to 1.0% weight:weight lubricant and the other components Teriflunomide, disintegrant, binder, acidic reacting compound and diluents show the same amount as defined under A) to C), E and F) above.

In a further embodiment the invention relates to a solid pharmaceutical composition comprising from about 3% to 20% weight:weight acidic reacting compound and the other components Teriflunomide, disintegrant, binder, lubricant and diluents show the same amount as defined under A) to D) and F) above.

Examples of acidic reacting compound are citric acid, acetic acid, glycolic acid, lactic acid, pyruvic acid, malonic acid, succinic acid, glutaric acid, fumaric acid, malic acid, tartaric acid, ascorbic acid, maleic acid, hydroxymaleic acid, benzoic acid, hydroxybenzoic acid, phenylacetic acid, cinnamic acid, salicyclic acid, 2-phenoxybenzoic acid, p-toluenesulfonic acid and sulfonic acids such as methanesulfonic acid and 2-hydroxyethanesulfonic acid or a mixture of one or more of said acidic reacting compound.

Teriflunomide is mixed with said disintegrant, binder, lubricant and diluents constituents to obtain the concentration of Teriflunomide and said further components according to the present invention in the final mixture and finally is mixed with an acidic reacting compound. In a further embodiment of the invention the solid pharmaceutical composition comprising components A) to F) as defined above shows a pH from 4.5 to 2.0, when water is adsorbed to the pharmaceutical composition or when water is added in small amounts to the pharmaceutical composition. In a further embodiment of the invention the solid pharmaceutical composition comprising components A) to F) as defined above shows a pH from about pH 3 to about pH 2.

The pH determination is performed by suspending one tablet in about 1 ml of purified water. The pH of the supernatant is determined with a pH sensitive probe.

In a further embodiment the invention relates to a solid pharmaceutical composition comprising a therapeutically effective amount of teriflunomide or a pharmaceutically acceptable basic addition salt thereof, wherein the pH of the solid pharmaceutical composition is less than about 4.5, particularly from about 4.5 to about 2.0, more particularly from about 3 to about 2.

In a further embodiment the invention relates to a solid pharmaceutical composition comprising A) about 1% to 20% weight:weight Teriflunomide, or a pharmaceutically acceptable basic addition salt thereof,
B) about 5% to 20% weight:weight disintegrant,
C) about 0% to 30% weight:weight binder,
D) about 0.1% to 2% weight:weight lubricant,
E) about 1% to 20% weight:weight acidic reacting compound,
F) about 0.1% to 0.5% weight:weight colloidal silicon dioxide and
G) the remaining percentage comprising diluents.

In a further embodiment the invention relates to a solid pharmaceutical composition comprising from about 2% to 15% weight:weight Teriflunomide and the other components disintegrant, binder, lubricant, acidic reacting compound, colloidal silicon dioxide and diluents show the same amount as defined under B) to G) above.

In a further embodiment the invention relates to a solid pharmaceutical composition comprising from about 7% to 15% weight:weight disintegrant and the other components Teriflunomide, binder, lubricant, acidic reacting compound, colloidal silicon dioxide and diluents show the same amount as defined under A) and C) to G) above.

In a further embodiment the invention relates to a solid pharmaceutical composition comprising from about 15% to 30% weight:weight binder and the other components Teriflunomide, disintegrant, lubricant, acidic reacting compound, colloidal silicon dioxide and diluents show the same amount as defined under A), B) and D) to G) above.

In a further embodiment the invention relates to a solid pharmaceutical composition comprising from about 0.1% to 1.0% weight:weight lubricant and the other components Teriflunomide, disintegrant, binder, acidic reacting compound, colloidal silicon dioxide and diluents show the same amount as defined under A) to C), E and G) above.

In a further embodiment the invention relates to a solid pharmaceutical composition comprising from about 3% to 20% weight:weight acidic reacting compound and the other components Teriflunomide, disintegrant, binder, lubricant, colloidal silicon dioxide and diluents show the same amount as defined under A) to D) and F) and G) above.

In a further embodiment the invention relates to a solid pharmaceutical composition comprising from about 0.2% to 0.4% weight:weight colloidal silicon dioxide and the other components Teriflunomide, disintegrant, binder, lubricant, acidic reacting compound and diluents show the same amount as defined under A) to E) and G) above.

In a further embodiment the invention relates to a solid pharmaceutical composition comprising from about 0.3% weight:weight colloidal silicon dioxide and the other components Teriflunomide, disintegrant, binder, lubricant, acidic reacting compound and diluents show the same amount as defined under A) to E) and G) above.

Teriflunomide is mixed with said disintegrant, binder, lubricant, colloidal silicon dioxide and diluents constituents to obtain the concentration of Teriflunomide and said further components according to the present invention in the final mixture and finally is mixed with an acidic reacting compound. In a further embodiment of the invention the solid pharmaceutical composition comprising components A) to G) as defined above shows a pH from 4.5 to 2.0, when water is adsorbed to the pharmaceutical composition or when water is added in small amounts to the pharmaceutical composition. In a further embodiment of the invention the solid pharmaceutical composition comprising components A) to G) as defined above shows a pH from about pH 3 to about pH 2.

In providing Teriflunomide formulations in forms suitable for unit dosage formation, the Teriflunomide and the further components of the solid pharmaceutical composition according to the invention can be mixed as powders. This mixing can be carried out using any of the mixing techniques known in the art. The mixing is preferably carried out using a high shear mixer, V-blender (or other twin-shell blender), bin blender or Turbula mixer-shaker. Blending is typically carried out first without the addition of a lubricant for sufficient time to assure complete mixing. At that point, the lubricant is typically added followed by a short (about 1-10 minute) further mixing period. Once the blend is made, unit dosage forms are prepared by procedures known in the art. Preferably, unit dosage forms are made on rotary tablet presses or capsule filling machines. The dosage forms thus prepared can then optionally be coated with a film designed to provide ease of swallowing, a proprietary or identification appearance and/or protection of the dosage form.

Alternatively, preferred processes for preparing a wet granulation of Teriflunomide and the further components of the solid pharmaceutical composition comprise the following steps:
(a) blending of the Teriflunomide with diluent and optionally some or all of the remaining excipients needed for the final composition. These other excipients can include binders, disintegrant, lubricant, acidic reacting compound and colloidal silica;
(b) adding a granulation solvent while the material from step (a) is under shear. Preferred granulation solvents include, water, ethanol, isopropanol and combinations thereof. Other ingredients can be added to the granulation solvent as known in the art. Examples of such additives are binders, acidic reacting compounds, wetting agents, stabilizers and buffers. The solvent can be applied by any technique known in the art. Preferred methods of applying the solvent while imparting shear include high shear granulation, low shear granulation, fluid bed granulation and extrusion granulation;
(c) optionally, the material from step (b) can be milled, ground or sieved. This wet material is then dried, preferably using air drying, fluid bed drying, oven drying or microwave drying. The drying is preferably carried out such that the drying temperature does not exceed about 60° C.;
(d) optionally this material is then milled or sieved;
(e) the material is then blended with additional excipients; and
(f) the composition is optionally formed into a unit dosage form, preferably a tablet or a capsule.

The dosage forms thus prepared can then optionally be coated with a film designed to provide ease of swallowing, a proprietary or identification appearance and/or protection of the dosage form.

The final dosage form is then packaged using procedures known in the art. For the present invention, the packaging is preferably in the form of foil-foil cold form blisters, plastic blisters or sealed bottles with or without desiccant. For blisters packaging materials with a water vapor permeability below 0.25 g/m$^2$/day are preferred.

In a further embodiment the invention relates to a solid pharmaceutical composition comprising a therapeutically effective amount of teriflunomide or a pharmaceutically acceptable basic addition salt thereof, wherein the solid pharmaceutical composition contains no more than about 0.1%, or particularly no more than about 0.05% by weight of 2-cyano-N-(4-trifluoromethyl-phenyl)-acetamide after being stored at about 25° C. and about 65% relative humidity for about 12 months.

In a further embodiment the invention relates to a solid pharmaceutical composition comprising a therapeutically effective amount of teriflunomide or a pharmaceutically acceptable basic addition salt thereof, wherein the solid pharmaceutical composition contains no more than about 0.3%, or particularly no more than about 0.2%, or more particularly no more than about 0.05% by weight of 2-cyano-N-(4-trifluoromethyl-phenyl)-acetamide after being stored at about 25° C. and about 65% relative humidity for about 36 months.

In a further embodiment the invention relates to a solid pharmaceutical composition comprising a therapeutically effective amount of teriflunomide or a pharmaceutically acceptable basic addition salt thereof, wherein the solid pharmaceutical composition contains no more than about 0.3%, particularly no more than about 0.1%, or more particularly no more than about 0.05% by weight of 2-cyano-N-(4-trifluoromethyl-phenyl)-acetamide after being stored at about 30° C. and about 65% relative humidity for about 12 months.

In a further embodiment the invention relates to a solid pharmaceutical composition comprising a therapeutically effective amount of teriflunomide or a pharmaceutically acceptable basic addition salt thereof, wherein the solid pharmaceutical composition contains no more than about 1%, or particularly no more than about 0.5%, or more particularly no more than about 0.05% by weight of 2-cyano-N-(4-trifluoromethyl-phenyl)-acetamide after being stored at about 30° C. and about 65% relative humidity for about 36 months.

In a further embodiment the invention relates to a solid pharmaceutical composition comprising a therapeutically effective amount of teriflunomide or a pharmaceutically acceptable basic addition salt thereof, wherein the solid pharmaceutical composition contains no more than about 0.3%, particularly no more than about 0.1%, or more particularly no more than about 0.05% by weight of 2-cyano-N-(4-trifluoromethyl-phenyl)-acetamide after being stored at about 30° C. and about 75% relative humidity for about 12 months.

The solid pharmaceutical composition according to the invention can be administered in any form or mode which makes the compound bioavailable in therapeutically effective amounts, including orally, sublingually, buccally, transdermally, intranasally, rectally, topically, and the like. One skilled in the art of preparing formulations can determine the proper form and mode of administration depending upon the particular characteristic disease to be treated, the stage of the disease, the condition of the patient and other relevant circumstances. For example, see Remington's Pharmaceutical Sciences, 18th Edition, Mack Publishing Co. (1990).

The solid pharmaceutical composition according to the invention may be administered orally, for example, in the form of tablets, troches, capsules, wafers, chewing gums and the like.

Other dosage unit forms may contain other various materials, which modify the physical form of the dosage unit, for example, as coatings. Thus, tablets or pills may be coated with nonfunctional coatings like Hypromelose based coatings, sugar, shellac, or other enteric coating agents.

The dosage range at which Teriflunomide exhibits its ability to act therapeutically can vary depending upon its severity, the patient, other underlying disease states that the patient is suffering from, and other medications that may be concurrently administered to the patient. Generally, Teriflunomide will exhibit their therapeutic activities at dosages of between about 0.001 mg/kg of patient body weight/day to about 100 mg/kg of patient body weight/day.

The solid pharmaceutical composition according to the invention is suitable for example, for treating acute immunological events, such as sepsis, allergy, graft-versus-host-reactions and host-versus-graft-reactions, Autoimmune disease such as rheumatoid arthritis, systemic lupus erythematodes, or multiple sclerosis, psoriasis, asthma, urticaria, rhinitis and uveitis, cancerous diseases such as lung cancer, leukemia, ovarian cancer, sarcoma, Kaposi's sarcoma, meningioma, intestinal cancer, lymph node cancer, brain tumours, breast cancer, pancreatic cancer, prostate cancer or skin cancer.

The following non-limiting examples illustrate the inventors' preferred methods for preparing and using the pharmaceutical compositions of the present invention.

EXAMPLES

Example 1

Manufacturing Process

Granulation Liquid:

Hydroxypropyl cellulose 7.5 mPa*s (HPC) and Citric acid monohydrate are dissolved in 219.3 g of purified water and are stirred for at least 30 min. The concentration of HPC in the final solution is 6.4% relative to the mass of water irrespective of the amount of citric acid added. (table 1).

TABLE 1

Compositions of granulation liquid

| Mass Citric acid/tablet | Mass Citric Acid [g] | Mass Hydorxypropyl Cellulose [g] | Mass water [g] | Total mass [g] |
|---|---|---|---|---|
| 0 mg Citric Acid | 0 | 14 | 219.3 | 233.3 |
| 2.5 mg Citric acid | 10 | 14 | 219.3 | 243.3 |
| 5 mg Citric acid | 20 | 14 | 219.3 | 253.3 |
| 20 mg Citric acid | 80 | 14 | 219.3 | 313.3 |
| 25 mg Citric acid | 100 | 14 | 219.3 | 333.3 |

Tablets:

1. Teriflunomide, Lactose or Mannitol (0C and 0D), Corn starch and if necessary citric acid monohydrate (1D and 1J) are blended for 5 min in a fluid bed granulator (UNI-Glatt, flap 25%, inlet air temperature ~23° C., shaking interval 30 sec, shaking 5 sec).
2. The resulting blend is granulated with a solution of HPC and if necessary citric acid in a fluid bed granulator (UNI Glatt, flap 25-30%, inlet air temperature 60° C., shaking interval 60 sec, shaking 5 sec, spray rate ~12.5 g/min, atomizing air pressure 1 bar, nozzle diameter 0.8 mm). Duration approx. 25 min
3. The granules are dried in a fluid bed granulator for approx. 20 min (UNI Glatt, flap 25-30%, inlet air temperature 60° C., shaking interval 60 sec, shaking 5 sec).
4. The granules are calibrated through a 1 mm sieve and are lubricated with microcrystalline cellulose, sodium starch glycollate and if necessary with colloidal silicon dioxide (Examples 1F-1J) in a turbula blender [2 L glass container] for 5 min.
5. After addition of Magnesium stearate the mixture is blended for another minute in a turbula blender [2 L glass container].

The final blend is compressed to tablets on a Korsch EKO single punch press. The composition of the solid pharmaceutical compositions prepared is given in tables 1, 2 and 3.

TABLE 1

Composition of Teriflunomide tablets with and without colloidal silicon dioxide (0A to 0E)

| | Example | | | | |
|---|---|---|---|---|---|
| | 0A | 0B | 0C | 0D | 0E |
| Teriflunomide [mg] | 7.000 | 7.000 | 7.000 | 7.000 | 14.000 |
| Lactose mono-hydrate [mg] | 81.000 | 81.000 | xx | xx | 76.000 |
| Mannitol [mg] | xx | xx | 101.0 | 101.0 | xx |
| Corn starch [mg] | 40.000 | 40.000 | 20.00 | 20.00 | 38.00 |
| Hydroxypropyl cellulose [mg] | 3.500 | 3.500 | 3.500 | 3.500 | 3.500 |
| Mass granules [mg] | 131.500 | 131.500 | 131.500 | 131.500 | 131.500 |
| Microcrystalline Cellulose [mg] | 10.500 | 10.000 | 10.000 | 10.500 | 10.500 |
| Sodium starch glycolate [mg] | 7.500 | 7.500 | 7.500 | 7.500 | 7.500 |
| Colloidal silicon dioxide [mg] | xx | 0.500 | 0.500 | xx | xx |
| Magnesium stearate [mg] | 0.500 | 0.500 | 0.500 | 0.500 | 0.500 |
| Total mass [mg] | 150.000 | 150.000 | 150.000 | 150.000 | 150.000 |

In the above table "xx" means no addition of the component

TABLE 2

Composition of Teriflunomide tablets acidified with Citric acid and without colloidal silicon dioxide

| | Example | | | |
|---|---|---|---|---|
| | 1A | 1B | 1C | 1D |
| Teriflunomide [mg] | 7.000 | 7.000 | 7.000 | 7.000 |
| Lactose mono-hydrate [mg] | 78.500 | 78.000 | 65.000 | 65.000 |
| Corn starch [mg] | 40.000 | 38.000 | 31.000 | 31.000 |
| Citric acid (solid) [mg] | xx | xx | xx | 5.000 |
| Citric acid (dissolved) [mg] | 2.500 | 5.000 | 25.000 | 20.000 |
| Hydroxypropyl cellulose [mg] | 3.500 | 3.500 | 3.500 | 3.500 |
| Mass granules [mg] | 131.500 | 131.500 | 131.500 | 131.500 |
| Microcrystalline Cellulose [mg] | 10.500 | 10.500 | 10.500 | 10.500 |
| Sodium starch glycolate [mg] | 7.500 | 7.500 | 7.500 | 7.500 |
| Colloidal silicon dioxide [mg] | xx | xx | xx | xx |
| Magnesium stearate [mg] | | 0.500 | 0.500 | 0.500 |
| Total mass [mg] | 150.000 | 150.000 | 150.000 | 150.000 |
| pH of tablet | 3.3 | 2.9 | 2.2 | 2.2 |

In the above table "xx" means no addition of the component

TABLE 3

Composition of Teriflunomide tablets acidified with citric acid and with colloidal silicon dioxide

| | Example | | | |
|---|---|---|---|---|
| | 1G | 1H | 1I | 1J |
| Teriflunomide [mg] | 7.000 | 7.000 | 7.000 | 7.000 |
| Lactose mono-hydrate [mg] | 78.500 | 78.000 | 65.000 | 65.000 |
| Corn starch [mg] | 40.000 | 38.000 | 31.000 | 31.000 |
| Citric acid (solid) [mg] | xx | xx | xx | 5.000 |
| Citric acid (dissolved) [mg] | 2.500 | 5.000 | 25.000 | 20.000 |
| Hydroxypropyl cellulose [mg] | 3.500 | 3.500 | 3.500 | 3.500 |

TABLE 3-continued

Composition of Teriflunomide tablets acidified with citric acid and with colloidal silicon dioxide

| | Example | | | |
|---|---|---|---|---|
| | 1G | 1H | 1I | 1J |
| Mass granules [mg] | 131.500 | 131.500 | 131.500 | 131.500 |
| Microcrystalline Cellulose [mg] | 10.000 | 10.000 | 10.000 | 10.000 |
| Sodium starch glycollate [mg] | 7.500 | 7.500 | 7.500 | 7.500 |
| Colloidal silicon dioxide [mg] | 0.500 | 0.500 | 0.500 | 0.500 |
| Magnesium stearate [mg] | 0.500 | 0.500 | 0.500 | 0.500 |
| Total mass [mg] | 150.000 | 150.000 | 150.000 | 150.000 |
| pH of tablet | 3.5 | 2.9 | 2.1 | 2.1 |

In the above table "xx" means no addition of the component

Example 2

Formation of 2-cyano-N-(4-trifluoromethyl-phenyl)-acetamide (A) Manufacturing of the Tablets The tablets are prepared according to the manufacturing process given in example 1. The composition of the tablets is given in tables 1, 2 and 3.

Storage of the Tablets

The samples are stored for up to 6 months at 25° C./60% RH, 30° C./65% RH, 40° C./75% RH in induction sealed HDPE bottles [wide necked bottle, 45 mL, white, round with induction seal and child resistant screw cap] and at 40° C./75% RH in open glass bottles. Bottles are stored upright.

Analysis of the Samples

Tablets are analyzed for content by HPLC.

The content of 2-cyano-N-(4-trifluoromethyl-phenyl)-acetamide in tablets, acidified with citric acid with our without colloidal silicon dioxide, is given in table 4.

TABLE 4

Formation of 2-cyano-N-(4-trifluoromethyl-phenyl)-acetamide in tablets with and without colloidal silicon dioxide (0A and 0B) and in acidified tablets without colloidal silicon dioxide (1A to 1D)

| Month | Storage conditions | Example | | | | | |
|---|---|---|---|---|---|---|---|
| | | 1A | 1B | 1C | 1D | 0A | 0B (Reference) |
| | | 2-cyano-N-(4-trifluoromethyl-phenyl)-acetamide [%] | | | | | |
| 0 | Initial | | | | | | |
| | Mean | 0.0130 | 0.0105 | 0.0123 | 0.0111 | 0.0143 | 0.0302 |
| | RSD | 10.1030 | 14.718 | 3.5217 | 17.0451 | 3.5157 | 3.8501 |
| 1 | 40° C./75% RH | | | | | | |
| | Mean | 0.0383 | 0.0449 | 0.0699 | 0.0481 | 0.0353 | 0.0919 |
| | RSD | 0.7039 | 1.6998 | 33.095 | 0.6950 | 2.7145 | 1.7791 |
| 1 | 40° C./75% RH open | | | | | | |
| | Mean | 0.1360 | 0.1490 | 0.0664 | 0.0683 | 0.0863 | 0.1283 |
| | RSD | 0.9016 | 1.4720 | 1.7785 | 2.5879 | 2.3490 | 2.0459 |
| 3 | 25° C./60% RH | | | | | | |
| | Mean | 0.0274 | 0.0196 | 0.0267 | 0.0194 | 0.0242 | 0.0431 |
| | RSD | 14.7830 | 5.3867 | 4.8454 | 5.4754 | 2.4537 | 2.4995 |
| 3 | 30° C./65% RH | | | | | | |
| | Mean | 0.0378 | 0.0323 | 0.0438 | 0.0347 | 0.0351 | 0.0656 |
| | RSD | 8.8841 | 7.1005 | 3.4361 | 4.9873 | 7.4946 | 2.8880 |
| 3 | 40° C./75% RH | | | | | | |
| | Mean | 0.1390 | 0.1535 | 0.1091 | 0.1029 | 0.0807 | 0.1821 |
| | RSD | 1.7326 | 2.5300 | 1.6702 | 0.6768 | 5.4502 | 1.0879 |
| 3 | 40° C./75% RH, open | | | | | | |
| | Mean | 0.3006 | 0.3306 | 0.1509 | 0.1534 | 0.2107 | 0.2461 |
| | RSD | 0.5967 | 0.6505 | 1.2309 | 0.6459 | 1.9609 | 2.3632 |
| 6 | 25° C./60% RH | | | | | | |
| | Mean | 0.0645 | 0.0341 | 0.0500 | 0.0369 | 0.0411 | 0.0824 |
| | RSD | 4.3042 | 11.6345 | 4.5263 | 3.1312 | 3.6245 | 2.8094 |
| 6 | 30° C./65% RH | | | | | | |
| | Mean | 0.0414 | 0.0689 | 0.0645 | 0.0694 | 0.0562 | 0.1396 |
| | RSD | 7.4586 | 4.2140 | 2.5329 | 4.2497 | 8.4947 | 1.2221 |
| 6 | 40° C./75% RH | | | | | | |
| | Mean | 0.2920 | 0.3592 | 0.1846 | 0.1829 | 0.1542 | 0.4149 |
| | RSD | 2.2691 | 1.7286 | 1.5597 | 1.9427 | 2.0578 | 1.3660 |
| 6 | 40° C./75% RH open | | | | | | |
| | Mean | 0.6769 | 0.7200 | 0.2635 | 0.2799 | 0.4447 | 0.6194 |
| | RSD | 0.3538 | 0.5624 | 0.8745 | 0.9602 | 1.2102 | 0.8003 |

"RSD" means relative standard deviation ((standard deviation of array X) × 100/(average of array X) = relative standard deviation).
"RH" means relative humidity; the relative humidity of an air-water mixture is defined as the ratio of the partial pressure of water vapor in the mixture to the saturated vapor pressure of water at a prescribed temperature.
In each batch 4 samples are determined at the beginning (0 month) after 1, 3 and 6 months. Only mean and RSD of the tested samples are shown.

The content of 2-cyano-N-(4-trifluoromethyl-phenyl)-acetamide in tablets acidified with citric acid with colloidal silicon dioxide is given in table 5.

TABLE 5

Formation of 2-cyano-N-(4-trifluoromethyl-phenyl)-acetamide in acidified tablets with colloidal silicon dioxide.

| | | Example | | | |
|---|---|---|---|---|---|
| | | 1G | 1H | 1I | 1J |
| Month | Storage conditions | 2-cyano-N-(4-trifluoromethyl-phenyl)-acetamide [%] | | | |
| 0 | Initial | | | | |
| | Mean | 0.0273 | 0.0215 | 0.0116 | 0.0120 |
| | RSD | 1.5419 | 10.1026 | 7.7747 | 2.1246 |
| 1 | 40° C./75% RH | | | | |
| | Mean | 0.0741 | 0.0704 | 0.0322 | 0.0416 |
| | RSD | 1.3713 | 5.4415 | 5.6604 | 1.2491 |
| 1 | 40° C./75% RH open | | | | |
| | Mean | 0.1561 | 0.1683 | 0.0616 | 0.0692 |
| | RSD | 1.1244 | 1.3425 | 0.9626 | 4.3785 |
| 3 | 25° C./60% RH | | | | |
| | Mean | 0.0356 | 0.0303 | 0.0140 | 0.0171 |
| | RSD | 5.9774 | 9.5942 | 5.4163 | 7.1324 |
| 3 | 30° C./65% RH | | | | |
| | Mean | 0.0496 | 0.0461 | 0.0232 | 0.0261 |
| | RSD | 5.4842 | 12.4861 | 6.2709 | 6.3572 |
| 3 | 40° C./75% RH | | | | |
| | Mean | 0.1558 | 0.1664 | 0.0715 | 0.0867 |
| | RSD | 2.8099 | 2.1597 | 1.6357 | 3.4267 |
| 3 | 40° C./75% RH, open | | | | |
| | Mean | 0.3061 | 0.3181 | 0.1198 | 0.1346 |
| | RSD | 0.9992 | 1.2165 | 3.0218 | 2.1899 |
| 6 | 25° C./60% RH | | | | |
| | Mean | 0.0703 | 0.0650 | 0.0274 | 0.0362 |
| | RSD | 2.1623 | 1.1513 | 3.6860 | 6.7916 |
| 6 | 30° C./65% RH | | | | |
| | Mean | 0.1099 | 0.1144 | 0.0511 | 0.0513 |
| | RSD | 2.0462 | 2.1572 | 3.0849 | 5.2812 |
| 6 | 40° C./75% RH | | | | |
| | Mean | 0.3751 | 0.4286 | 0.1627 | 0.1768 |
| | RSD | 1.0971 | 1.0910 | 1.1734 | 0.4281 |
| 6 | 40° C./75% RH open | | | | |
| | Mean | 0.7496 | 0.7840 | 0.2765 | 0.2941 |
| | RSD | 0.1725 | 0.6620 | 1.0646 | 0.4167 |

In each batch 4 samples are determined at the beginning (0 month), after 1, 3 and 6 months. Only mean and RSD of the tested samples are shown.

After 3 or 6 months storage at the above-identified storage conditions in HDPE bottles Teriflunomide tablets containing 25 mg citric acid lubricated with or without colloidal silicon dioxide [Examples 1C, D, I, J] and Teriflunomide tablets containing no citric acid but lubricated without colloidal silicon dioxide (Example 0A) display significantly reduced formation of 2-cyano-N-(4-trifluoromethyl-phenyl)-acetamide compared to Teriflunomide tablets containing colloidal silicon dioxide (Example 0B). In induction sealed HDPE bottles, the stabilizing effect of citric acid is more pronounced in the presence of colloidal silicon dioxide.

The determination of Teriflunomide, 2-cyano-N-(4-trifluoromethyl-phenyl)-acetamide and 4-TFMA are performed by a gradient high performance liquid chromatographic system (HPLC) as follows:
Stationary phase: Purospher STAR RP18e (3 µm)
Column material: stainless steel
Column length: 125 mm
Column internal diameter: 4.0 mm
Equilibration of the column: Column must be rinsed with the mobile phase B for at least 15 min at a flow rate of 1.0 mL/min Mobile Phase
Buffer is prepared by the transfer of 50 mmol (4.2 g) of sodium acetate, 50 mmol (2.9 g) of sodium chloride in a glass bottle for mobile phases and addition of 1000 mL water. Adjust pH to 6.5 with glacial acetic acid using a pH-meter.

| Mobile phase A | | Mobile phase B | |
|---|---|---|---|
| Buffer pH 6.5 | 900 mL | Buffer pH 6.5 | 100 mL |
| Acetonitrile | 100 mL | Acetonitrile | 900 mL |

Gradient:

| Time [minutes] | Mobile phase A [%] | Mobile phase B [%] |
|---|---|---|
| 0 | 100 | 0 |
| 0 to 20 | 52 | 48 |
| 20 to 25 | 0 | 100 |
| 25 to 26 | 100 | 0 |
| 26 to 30 | 100 | 0 |

Procedure
Flow rate: 1.0 mL/minute
Expected pressure drop: 220 bar
Injection volume: 10 µL
Auto sampler temperature: Set auto sampler temperature at +15° C.
Column temperature: Set oven temperature at +20° C.
Detection: 249 nm (UV)
Typical reporting time: 25 minutes
Typical total run time: 30 minutes
Retention times:
Teriflunomide about 15.0 minutes
2-Cyano-N-(4-trifluoromethyl-phenyl)-acetamide about 19.3 minutes
4-TFMA about 19.8 minutes Example 3 pH Determination of the Tablets

The pH determination is performed by suspending one tablet in about 1 ml of purified water. After disintegration of the tablet and settling of the solid contents, the pH of the supernatant is determined with a pH sensitive probe. The mean result of two individual tablets is reported as pH of tablet (see tables 2 and 3).

Example 4

Formation of
2-cyano-N-(4-trifluoromethyl-phenyl)-acetamide and
4-TFMA in Teriflunomide Tablets With and Without
Colloidal Silicon Dioxide Manufacturing of the Tablets
The tablets are prepared according to the manufacturing process given in example 1. The composition of the tablets is given in table 1.
Storage of the Tablets
In an additional stability study the samples are stored for 6 months at 40° C./75% RH in induction sealed HDPE bottles [wide necked bottle, 60 mL, white, round with induction seal and child resistant screw cap]. Bottles are stored upright.

Analysis of the Samples

Tablets are analyzed for related impurities by HPLC (using the method described above).

The content of 2-cyano-N-(4-trifluoromethyl-phenyl)-acetamide and of 4-TFMA after 6 month storage at 40° C./75% RH in tablets with or without colloidal silicon dioxide is given in table 6.

TABLE 6

Formation of 2-cyano-N-(4-trifluoromethyl-phenyl)-acetamide and of 4-TFMA in tablets with and without colloidal silicon dioxide (0A and 0B)

| Month | Storage conditions | Example |  |  |  |
|---|---|---|---|---|---|
|  |  | 0A | 0B | 0C | 0D |
|  |  | 2-cyano-N-(4-trifluoromethyl-phenyl)-acetamide [%] | | | |
| 0 | Initial | | | | |
|  | Mean | 0.004 | 0.013 | 0.008 | 0.002 |
|  | RSD | 0.191 | 0.026 | 0.010 | 0.320 |
| 6 | 40° C./75% RH | | | | |
|  | Mean | 0.213 | 0.543 | 0.600 | 0.241 |
|  | RSD | 0.006 | 0.001 | 0.001 | 0.001 |
|  |  | 4-TFMA [ppm] | | | |
| 0 | Initial | | | | |
|  | Mean | 0.00 | 0.00 | 0.00 | 0.00 |
|  | RSD | — | — | — | — |
| 6 | 40° C./75% RH | | | | |
|  | Mean | 28 | 57 | 48 | 22 |
|  | RSD | 0.049 | 0.035 | 0.244 | 0.050 |

After 6 months storage at the above-identified storage conditions in HDPE bottles Teriflunomide tablets lubricated without colloidal silicon dioxide (Example 0A and 0D) display significantly reduced formation of 2-cyano-N-(4-trifluoromethyl-phenyl)-acetamide compared to Teriflunomide tablets containing colloidal silicon dioxide (Example 0B and 0C). Further more the formation of 4-TFMA is strongly reduced in tablets containing no colloidal silicon dioxide (Example 0A and 0D) compared to tablets lubricated with colloidal silicon dioxide ((Example 0B and 0C).

The determination of Teriflunomide and 2-cyano-N-(4-trifluoromethyl-phenyl)-acetamide and 4-TFMA are performed by a gradient high performance liquid chromatographic system (HPLC) as described in Example 2.

Example 5

Formation of 2-cyano-N-(4-trifluoromethyl-phenyl)-acetamide and 4-TFMA in Film-Coated Tablet The samples of example 0A and 0E are made into hypromelose based, i.e. Opadry® or Spectrablend™ (5 mg/tablet) film-coated tablets and stored for up to 36 months at 30° C./65% RH, 30° C./75% RH and 40° C./75% RH in:

ALU/PVC blisters (i.e. PVC (Polyvinyl chloride) 250 µm & Aluminium sealing foil [20 µm, with PVC/acrylate heat sealable coating]);

ALU/PVdC blisters (i.e. bilayer film of PVC (Polyvinyl chloride) 250 µm and 90 g/m² vinylidene chloride and acrylic acid methylester Copolymer & Aluminium sealing foil [20 µm, with PVC/acrylate heat sealable coating]);

ALU/PVC/PCTFE blisters (i.e. 254 µm PVC/75 µm PCTFE laminated film & Aluminium sealing foil [20 µm, with PVC/acrylate heat sealable coating]);

ALU/ALU blisters (i.e. PVC 60 µm/Aluminium foil 45 µm/Polyamide 25 µm & Aluminium foil [20 µm with PVC/acrylate heat sealable coating]); or HDPE bottles (i.e. high density polyethylene bottles with polypropylene cap and aluminium induction seal and with or without silica gel desiccant canister added).

TABLE 7

Formation of 2-cyano-N-(4-trifluoromethyl-phenyl)-acetamide [%] of film-coated tablet up to 12 months storage

| Example | Packaging | Storage Condition | 12 Months |
|---|---|---|---|
| 0A | ALU/PVC | 30° C./65% RH | 0.29% |
| 0A | ALU/PVdC | 30° C./75% RH | 0.21% |
| 0A | HDPE 60 mL | 30° C./75% RH | 0.09% |
| 0A | HDPE 45 mL/desiccant | 30° C./65% RH | 0.06% |
|  |  | 30° C./75% RH | 0.09% |
| 0A | ALU/PVC/PCTFE | 30° C./65% RH | 0.08% |
| 0A | ALU/ALU | 30° C./65% RH | 0.05% |
| 0E | ALU/PVC | 30° C./65% RH | 0.15% |
| 0E | ALU/PVdC | 30° C./75% RH | 0.12% |
| 0E | HDPE 60 mL | 30° C./75% RH | <0.05% |
| 0E | HDPE 45 mL/desiccant | 30° C./65% RH | <0.05% |
|  |  | 30° C./75% RH | <0.05% |
| 0E | ALU/PVC/PCTFE | 30° C./65% RH | <0.05% |
| 0E | ALU/ALU | 30° C./65% RH | <0.05% |

TABLE 8

Formation of 2-cyano-N-(4-trifluoromethyl-phenyl)-acetamide [%] of film-coated tablet up to 36 months storage

| Example | Packaging | Storage Condition | 36 Months |
|---|---|---|---|
| 0A | ALU/PVC | 30° C./65% RH | 0.94% |
| 0A | ALU/PVC/PCTFE | 30° C./65% RH | 0.41% |
| 0A | ALU/ALU | 30° C./65% RH | 0.20% |
| 0E | ALU/PVC | 30° C./65% RH | 0.52% |
| 0E | ALU/PVC/PCTFE | 30° C./65% RH | 0.21% |
| 0E | ALU/ALU | 30° C./65% RH | <0.05 |

4-TFMA levels for tablets reported in Tables 7 and 8 are all below 0.01%.

I claim:

1. A solid pharmaceutical composition comprising
   a) 1% to 30% weight:weight Teriflunomide, or a pharmaceutically acceptable basic addition salt thereof,
   b) 5% to 20% weight:weight disintegrant,
   c) 0% to 40% weight:weight binder,
   d) 0.1% to 2% weight:weight lubricant, and
   e) the remaining percentage comprising diluents;
wherein the solid pharmaceutical composition does not contain colloidal silicon dioxide.

2. The solid pharmaceutical composition according to claim 1 wherein said disintegrant is selected from the group consisting of carboxymethylcellulose, low substituted hydroxypropyl cellulose, microcrystalline cellulose, powdered cellulose, croscarmellose sodium, methylcellulose, polacrilin potassium, sodium alginate, and sodium starch glycolate or a mixture of one or more of said disintegrants.

3. The solid pharmaceutical composition according to claim 2 wherein said disintegrant is selected from the group consisting of low substituted hydroxypropyl cellulose, microcrystalline cellulose, powdered cellulose, croscarmellose sodium, and sodium starch glycolate or a mixture of one or more of said disintegrants.

4. The solid pharmaceutical composition according to claim 1 wherein said binder is selected from the group consisting of acacia, carboxymethylcellulose, hydroxyethylcellulose, hydroxypropylcellulose, dextrin, gelatin, guar gum, hydroxypropyl methylcellulose, maltodextrin, methylcellulose, sodium alginate, pregelatinized starch, starches and zein or a mixture of one or more of said binders.

5. The solid pharmaceutical composition according to claim 4 wherein said binder is selected from the group consisting of hydroxypropylcellulose, hydroxypropyl methylcellulose, pregelatinized starch, potato starch, corn starch, and cereal starch or a mixture of one or more of said binders.

6. The solid pharmaceutical composition according to claim 1 wherein said lubricant is selected from the group consisting of calcium stearate, glyceryl palmitostearate, sodium benzoate, sodium lauryl sulfate, sodium stearyl fumarate, stearic acid, talc, zinc stearate and magnesium stearate or a mixture of one or more of said lubricants.

7. The solid pharmaceutical composition according to claim 6 wherein said lubricant is selected from the group consisting of sodium stearyl fumarate and magnesium stearate or a mixture of one or more of said lubricants.

8. The solid pharmaceutical composition according to claim 1 wherein said diluent is selected from the group consisting of cellulose, cellulose acetate, dextrates, dextrin, dextrose, fructose, 1-O-α-D-Glucopyranosyl-D-mannitol, glyceryl palmitostearate, hydrogenated vegetable oil, kaolin, lactitol, lactose, lactose mono-hydrate, maltitol, mannitol, maltodextrin, maltose, pregelatinized starch, sodium chloride, sorbitol, starches, sucrose, talc and xylitol or a mixture of one or more of said diluents.

9. The solid pharmaceutical composition according to claim 8 wherein said diluent is selected from the group consisting of lactose, lactose mono-hydrate, mannitol and starches or a mixture of one or more of said diluents.

10. A solid pharmaceutical composition comprising a therapeutically effective amount of teriflunomide or a pharmaceutically acceptable basic addition salt thereof, wherein the pH of the solid pharmaceutical composition is no more than about 2.2.

11. The solid pharmaceutical composition according to claim 10, wherein the pH of the solid pharmaceutical composition is from about 2.2 to about 2.0.

12. The solid pharmaceutical composition according to claim 10 comprising
A) 1% to 20% weight:weight Teriflunomide, or a pharmaceutically acceptable basic addition salt thereof,
B) 5% to 20% weight:weight disintegrant,
C) 0% to 30% weight:weight binder,
D) 0.1% to 2% weight:weight lubricant,
E) 1% to 20% weight:weight acidic reacting compound wherein said acidic reacting compound is selected from the group consisting of citric acid, acetic acid, glycolic acid, lactic acid, pyruvic acid, malonic acid, succinic acid, glutaric acid, fumaric acid, malic acid, tartaric acid, ascorbic acid, maleic acid, hydroxymaleic acid, benzoic acid, hydroxybenzoic acid, phenylacetic acid, cinnamic acid, salicyclic acid, 2-phenoxybenzoic acid, p-toluenesulfonic acid, sulfonic acids, methanesulfonic acid and 2-hydroxyethanesulfonic acid or a mixture of one or more of said acidic reacting compounds and
F) the remaining percentage comprising diluents.

13. The solid pharmaceutical composition according to claim 12 wherein said disintegrant is selected from the group consisting of carboxymethylcellulose, low substituted hydroxypropyl cellulose, microcrystalline cellulose, powdered cellulose, croscarmellose sodium, methylcellulose, polacrilin potassium, sodium alginate, and sodium starch glycolate, or a mixture of one or more of said disintegrants.

14. The solid pharmaceutical composition according to claim 12 wherein said binder is selected from the group consisting of acacia, carboxymethylcellulose, hydroxyethylcellulose, hydroxypropylcellulose, dextrin, gelatin, guar gum, hydroxypropyl methylcellulose, maltodextrin, methylcellulose, pregelatinized starch, sodium alginate, starches, potato starch, corn starch or cereal starch and zein or a mixture of one or more of said binders.

15. The solid pharmaceutical composition according to claim 12 wherein said lubricant is selected from the group consisting of calcium stearate, glyceryl palmitostearate, sodium benzoate, sodium lauryl sulfate, sodium stearyl fumarate, stearic acid, talc, zinc stearate and magnesium stearate or a mixture of one or more of said lubricants.

16. The solid pharmaceutical composition according to claim 12 wherein said diluent is selected from the group consisting of cellulose, cellulose acetate, dextrates, dextrin, dextrose, fructose, 1-O-α-D-Glucopyranosyl-D-mannitol, glyceryl palmitostearate, hydrogenated vegetable oil, kaolin, lactitol, lactose, maltitol, mannitol, maltodextrin, maltose, pregelatinized starch, sodium chloride, sorbitol, starches, sucrose, talc and xylitol or a mixture of one or more of said diluents.

17. The solid pharmaceutical composition according to claim 12 further comprising about
0.1% to 0.5% weight:weight colloidal silicon dioxide.

18. A solid pharmaceutical composition comprising a therapeutically effective amount of teriflunomide or a pharmaceutically acceptable basic addition salt thereof, wherein the solid pharmaceutical composition does not contain colloidal silicon dioxide and the solid pharmaceutical composition contains no more than about 0.3% by weight of 2-cyano-N-(4-trifluoromethyl-phenyl)-acetamide after being stored at about 30° C. and about 65% relative humidity for about 12 months.

19. The solid pharmaceutical composition according to claim 18, which contains no more than about 0.1% by weight of 2-cyano-N-(4-trifluoromethyl-phenyl)-acetamide.

20. The solid pharmaceutical composition according to claim 18, which contains no more than about 0.05% by weight of 2-cyano-N-(4-trifluoromethyl-phenyl)-acetamide.

21. A solid pharmaceutical composition comprising a therapeutically effective amount of teriflunomide or a pharmaceutically acceptable basic addition salt thereof, wherein the solid pharmaceutical composition does not contain colloidal silicon dioxide and the solid pharmaceutical composition contains no more than about 1.0% by weight of 2-cyano-N-(4-trifluoromethyl-phenyl)-acetamide after being stored at about 30° C. and about 65% relative humidity for about 36 months.

22. The solid pharmaceutical composition according to claim 19, which contains no more than about 0.5% by weight of 2-cyano-N-(4-trifluoromethyl-phenyl)-acetamide.

23. The solid pharmaceutical composition according to claim 19, which contains no more than about 0.05% by weight of 2-cyano-N-(4-trifluoromethyl-phenyl)-acetamide.

24. A solid pharmaceutical composition comprising a therapeutically effective amount of teriflunomide or a pharmaceutically acceptable basic addition salt thereof, wherein the solid pharmaceutical composition does not contain colloidal silicon dioxide and the solid pharmaceutical composition contains no more than about 0.3% by weight of 2-cyano-N-(4-trifluoromethyl-phenyl)-acetamide after being stored at about 30° C. and about 75% relative humidity for about 12 months.

25. The solid pharmaceutical composition according to claim 24, which contains no more than about 0.1% by weight of 2-cyano-N-(4-trifluoromethyl-phenyl)-acetamide.

26. The solid pharmaceutical composition according to claim 24, which contains no more than about 0.05% by weight of 2-cyano-N-(4-trifluoromethyl-phenyl)-acetamide.

27. The solid pharmaceutical composition according to claim 1 comprising teriflunomide as the sole active ingredient.

28. The solid pharmaceutical composition according to claim 27 wherein said disintegrant is selected from the group consisting of carboxymethylcellulose, low substituted hydroxypropyl cellulose, microcrystalline cellulose, powdered cellulose, croscarmellose sodium, methylcellulose, polacrilin potassium, sodium alginate, and sodium starch glycolate or a mixture of one or more of said disintegrants.

29. The solid pharmaceutical composition according to claim 27 wherein said disintegrant is selected from the group consisting of low substituted hydroxypropyl cellulose, microcrystalline cellulose, powdered cellulose, croscarmellose sodium, and sodium starch glycolate or a mixture of one or more of said disintegrants.

30. The solid pharmaceutical composition according to claim 27 wherein said binder is selected from the group consisting of acacia, carboxymethylcellulose, hydroxyethylcellulose, hydroxypropylcellulose, dextrin, gelatin, guar gum, hydroxypropyl methylcellulose, maltodextrin, methylcellulose, sodium alginate, pregelatinized starch, starches and zein or a mixture of one or more of said binders.

31. The solid pharmaceutical composition according to claim 27 wherein said binder is selected from the group consisting of hydroxypropylcellulose, hydroxypropyl methylcellulose, pregelatinized starch, potato starch, corn starch or cereal starch or a mixture of one or more of said binders.

32. The solid pharmaceutical composition according to claim 27 wherein said lubricant is selected from the group consisting of calcium stearate, glyceryl palmitostearate, sodium benzoate, sodium lauryl sulfate, sodium stearyl fumarate, stearic acid, talc, zinc stearate and magnesium stearate or a mixture of one or more of said lubricants.

33. The solid pharmaceutical composition according to claim 27 wherein said lubricant is selected from the group consisting of sodium stearyl fumarate and magnesium stearate or a mixture of one or more of said lubricants.

34. The solid pharmaceutical composition according to claim 27 wherein said diluent is selected from the group consisting of cellulose, cellulose acetate, dextrates, dextrin, dextrose, fructose, 1-O-α-D-Glucopyranosyl-D-mannitol, glyceryl palmitostearate, hydrogenated vegetable oil, kaolin, lactitol, lactose, lactose mono-hydrate, maltitol, mannitol, maltodextrin, maltose, pregelatinized starch, sodium chloride, sorbitol, starches, sucrose, talc and xylitol or a mixture of one or more of said diluents.

35. The solid pharmaceutical composition according to claim 34 wherein said diluent is selected from the group consisting of lactose, lactose mono-hydrate, mannitol and starches or a mixture of one or more of said diluents.

36. The solid pharmaceutical composition according to claim 1, comprising about 7 mg of teriflunomide, about 81 mg of lactose monohydrate, about 40 mg of corn starch, about 3.5 mg of hydroxypropyl cellulose, about 10.5 mg of microcrystalline cellulose, about 7.5 mg of sodium starch glycolate and about 0.5 mg of magnesium stearate.

37. The solid pharmaceutical composition according to claim 1, comprising about 14 mg of teriflunomide, about 76 mg of lactose monohydrate, about 38 mg of corn starch, about 3.5 mg of hydroxypropyl cellulose, about 10.5 mg of microcrystalline cellulose, about 7.5 mg of sodium starch glycolate and about 0.5 mg of magnesium stearate.

* * * * *

UNITED STATES PATENT AND TRADEMARK OFFICE
CERTIFICATE OF CORRECTION

PATENT NO. : 8,802,735 B2  
APPLICATION NO. : 13/422494  
DATED : August 12, 2014  
INVENTOR(S) : Gerrit Hauck Page 1 of 2

It is certified that error appears in the above-identified patent and that said Letters Patent is hereby corrected as shown below:

On the Title page,

In item (54), in column 1, in "Title", line 2, delete "TRIFLUORMETHYLPHENYL" and insert -- TRIFLUOROMETHYLPHENYL --, therefor.

In item (56), in column 2, under "Other Publications", line 14, delete "Absorbtion" and insert -- Absorption --, therefor.

In item (56), in column 2, under "Other Publications", line 24, delete "Pharmacetics" and insert -- Pharmaceutics --, therefor.

In The Specification

In column 1, line 2, delete "TRIFLUORMETHYLPHENYL" and insert -- TRIFLUOROMETHYLPHENYL --, therefor.

In column 1, line 48, delete "Prkash" and insert -- Prakash --, therefor.

In column 2, line 28, delete "4-TFMA" and insert -- 4-TFMA. --, therefor.

In column 3, line 16, delete "Aeorsil" and insert -- Aerosil --, therefor.

In column 4, line 26, delete "hydroxyproyl cellulose," and insert -- hydroxypropylcellulose, --, therefor.

In column 4, line 54, delete "hydroxyproylcellulose" and insert -- hydroxypropylcellulose --, therefor.

In column 5, line 36, delete "salicyclic" and insert -- salicylic --, therefor.

In column 8, line 51, delete "Hypromelose" and insert -- Hypromellose --, therefor.

In column 9, line 29, delete "Hydorxypropyl" and insert -- Hydroxypropyl --, therefor.

In column 9, line 51, delete "min" and insert -- min. --, therefor.

In column 9, line 58, delete "glycollate" and insert -- glycolate --, therefor.

In column 10, line 46, in Table 2, after "[mg]" insert -- 0.500 --.

In column 11, line 12, delete "glycollate" and insert -- glycolate --, therefor.

Signed and Sealed this  
Twelfth Day of April, 2016

Michelle K. Lee  
*Director of the United States Patent and Trademark Office*

CERTIFICATE OF CORRECTION (continued)
U.S. Pat. No. 8,802,735 B2

In column 15, line 38, delete "Further more" and insert -- Furthermore --, therefor.

In column 15, line 54, delete "Hypromelose" and insert -- Hypromellose --, therefor.

In the Claims

In column 17, line 56, in claim 12, delete "salicyclic" and insert -- salicylic --, therefor.

In column 17, line 60, in claim 12, delete "diluents." and insert -- diluent. --, therefor.

In column 18, line 54, in claim 22, delete "19," and insert -- 21, --, therefor.

In column 18, line 57, in claim 23, delete "19," and insert -- 21, --, therefor.

In column 20, line 6, in claim 33, delete "27" and insert -- 32 --, therefor.